(12) United States Patent
Park et al.

(10) Patent No.: US 10,706,717 B2
(45) Date of Patent: *Jul. 7, 2020

(54) ELECTRONIC DEVICE AND CONTROL METHOD THEREOF

(71) Applicant: SAMSUNG ELECTRONICS CO., LTD., Suwon-si (KR)

(72) Inventors: Sang-bae Park, Suwon-si (KR); Hyun-jae Baek, Seoul (KR); Jae-geol Cho, Yongin-si (KR); Byung-hun Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/455,145

(22) Filed: Jun. 27, 2019

(65) Prior Publication Data

US 2019/0318617 A1  Oct. 17, 2019

Related U.S. Application Data

(63) Continuation of application No. 15/350,544, filed on Nov. 14, 2016, now Pat. No. 10,417,901.

(30) Foreign Application Priority Data

Jan. 26, 2016  (KR) .......................... 10-2016-0009382

(51) Int. Cl.
*G08C 19/16* (2006.01)
*G08C 17/02* (2006.01)
(Continued)

(52) U.S. Cl.
CPC .......... *G08C 17/02* (2013.01); *A61B 5/02416* (2013.01); *A61B 5/4812* (2013.01);
(Continued)

(58) Field of Classification Search
CPC ................ G08C 17/02; G08C 2201/12; G08C 2201/32; G08C 2201/51; A61B 5/02416;
(Continued)

(56) References Cited

U.S. PATENT DOCUMENTS 7,509,163 B1  3/2009  Luo et al.
9,641,239 B2  5/2017  Panther et al.
(Continued)

FOREIGN PATENT DOCUMENTS

JP  2013202121 A  10/2013
JP  2014195710 A  10/2014
(Continued)

OTHER PUBLICATIONS

Communication dated Oct. 9, 2018, issued by the European Patent Office in counterpart European Application No. 17744506.1.
(Continued)

*Primary Examiner* — Kerri L McNally
*Assistant Examiner* — Thang D Tran
(74) *Attorney, Agent, or Firm* — Sughrue Mion, PLLC

(57) ABSTRACT

A device includes a first sensor to generate a movement signal of a user movement; a second sensor to generate a PPG signal of the user; and a processor configured to set each of time periods as a predetermined amount of time to determine one sleeping state of the user, set a first part of the predetermined amount of time in each time period to emit the light, and set a remaining part of the predetermined amount of time in each time period to not emit the light, control the light emitter of the second sensor to emit the light in the first part of each time period and to not emit the light in the remaining part of each time period, and determine, for each time period, the sleeping state of the user based on the movement signal and the PPG signal that are generated for each time period.

18 Claims, 13 Drawing Sheets

(51) Int. Cl.
*A61B 5/024* (2006.01)
*A61B 5/00* (2006.01)

(52) U.S. Cl.
CPC .......... *A61B 5/6801* (2013.01); *A61B 5/6892* (2013.01); *A61B 2562/0219* (2013.01); *A61B 2562/0223* (2013.01); *A61B 2562/0247* (2013.01); *G08C 2201/12* (2013.01); *G08C 2201/32* (2013.01); *G08C 2201/51* (2013.01)

(58) Field of Classification Search
CPC ... A61B 5/4812; A61B 5/6801; A61B 5/6892; A61B 2562/0219; A61B 2562/0223; A61B 2562/0247
USPC .......................................................... 340/12.5
See application file for complete search history.

(56) References Cited

U.S. PATENT DOCUMENTS

| | | | | |
|---|---|---|---|---|
| 10,165,633 | B2* | 12/2018 | Furukawa | G09G 3/342 |
| 2004/0150372 | A1* | 8/2004 | Lee | H02J 7/0031 320/148 |
| 2007/0013344 | A1* | 1/2007 | Aradachi | G01R 31/3648 320/132 |
| 2007/0015976 | A1 | 1/2007 | Miesel et al. | |
| 2008/0074357 | A1* | 3/2008 | Kanda | G09G 3/3233 345/76 |
| 2009/0264715 | A1 | 10/2009 | Auphan | |
| 2010/0113898 | A1 | 5/2010 | Kim et al. | |
| 2010/0179469 | A1* | 7/2010 | Hammond | A61N 5/0603 604/20 |
| 2010/0283618 | A1 | 11/2010 | Wolfe et al. | |
| 2010/0286494 | A1 | 11/2010 | Addison et al. | |
| 2011/0267196 | A1* | 11/2011 | Hu | A61B 5/0002 340/575 |
| 2012/0083705 | A1* | 4/2012 | Yuen | A61B 5/0002 600/508 |
| 2012/0286675 | A1* | 11/2012 | Carmen | G05B 19/00 315/158 |
| 2013/0178919 | A1 | 7/2013 | MeNeill | |
| 2013/0267791 | A1* | 10/2013 | Halperin | A61B 5/002 600/300 |
| 2014/0073486 | A1 | 3/2014 | Ahmed et al. | |
| 2014/0088378 | A1 | 3/2014 | Muzet | |
| 2014/0135612 | A1* | 5/2014 | Yuen | A61B 5/02405 600/407 |
| 2014/0206954 | A1 | 7/2014 | Yuen et al. | |
| 2014/0269223 | A1* | 9/2014 | Mokhnatkina | G04G 13/02 368/73 |
| 2014/0273858 | A1 | 9/2014 | Panther et al. | |
| 2014/0275850 | A1* | 9/2014 | Venkatraman | A61B 5/0002 600/301 |
| 2014/0275852 | A1* | 9/2014 | Hong | A61B 5/02427 600/301 |
| 2014/0278220 | A1 | 9/2014 | Yuen | |
| 2014/0278229 | A1* | 9/2014 | Hong | A63B 71/06 702/160 |
| 2014/0288390 | A1 | 9/2014 | Hong et al. | |
| 2014/0288392 | A1 | 9/2014 | Hong et al. | |
| 2014/0288435 | A1 | 9/2014 | Richards et al. | |
| 2015/0026647 | A1* | 1/2015 | Park | G06F 3/0488 715/863 |
| 2015/0036573 | A1 | 2/2015 | Malik et al. | |
| 2015/0164238 | A1* | 6/2015 | Benson | G16H 50/30 340/540 |
| 2015/0173671 | A1* | 6/2015 | Paalasmaa | A61B 5/0022 600/301 |
| 2015/0186609 | A1 | 7/2015 | Utter, II | |
| 2015/0190087 | A1* | 7/2015 | Shinar | G16H 40/60 600/301 |
| 2015/0230750 | A1 | 8/2015 | McDarby et al. | |
| 2015/0257220 | A1* | 9/2015 | Furukawa | G09G 3/342 315/224 |
| 2015/0258301 | A1* | 9/2015 | Trivedi | G06F 16/636 600/28 |
| 2015/0345985 | A1 | 12/2015 | Fung et al. | |
| 2015/0351556 | A1* | 12/2015 | Franceschetti | G16H 40/67 5/421 |
| 2015/0371028 | A1 | 12/2015 | Patel et al. | |
| 2016/0007916 | A1* | 1/2016 | Iwawaki | A61B 5/02055 600/301 |
| 2016/0007934 | A1* | 1/2016 | Arnold | A61B 5/1123 600/595 |
| 2016/0015314 | A1 | 1/2016 | Dusanter et al. | |
| 2016/0029911 | A1 | 2/2016 | Lee | |
| 2016/0051158 | A1* | 2/2016 | Silva | A61B 5/02416 600/479 |
| 2016/0051201 | A1* | 2/2016 | Maani | A61B 5/721 600/301 |
| 2016/0058429 | A1 | 3/2016 | Shinar et al. | |
| 2016/0066844 | A1* | 3/2016 | Venkatraman | A61B 5/0002 702/141 |
| 2016/0157773 | A1 | 6/2016 | Baek et al. | |
| 2016/0262690 | A1* | 9/2016 | Chen | A61B 5/4815 |
| 2016/0287181 | A1* | 10/2016 | Han | A61B 5/7214 |
| 2016/0313176 | A1* | 10/2016 | Lee | G01J 1/429 |
| 2017/0011210 | A1* | 1/2017 | Cheong | G06F 3/017 |
| 2017/0231490 | A1* | 8/2017 | Toth | A61B 5/40 600/558 |
| 2017/0273612 | A1* | 9/2017 | Kim | G06Q 50/22 |
| 2017/0347948 | A1* | 12/2017 | Thein | A61B 5/02405 |

FOREIGN PATENT DOCUMENTS

| | | |
|---|---|---|
| KR | 1020140070127 A | 6/2014 |
| WO | 2014068537 A2 | 5/2014 |
| WO | 2015/127142 A1 | 8/2015 |

OTHER PUBLICATIONS

International Search Report, issued by International Searching Authority in corresponding International Application No. PCT/KR2017/000645, dated Apr. 26, 2017, (PCT/ISA/210).

Written Opinion, issued by International Searching Authority in corresponding International Application No. PCT/KR2017/000645, dated Apr. 26, 2017, (PCT/ISA/237).

Office Action received in parent U.S. Appl. No. 15/350,544 dated May 9, 2017.

Office Action received in parent U.S. Appl. No. 15/350,544 dated Nov. 6, 2017.

Office Action received in parent U.S. Appl. No. 15/350,544 dated Mar. 14, 2018.

Office Action received in parent U.S. Appl. No. 15/350,544 dated Jul. 27, 2018.

Office Action received in parent U.S. Appl. No. 15/350,544 dated Nov. 13, 2018.

Notice of Allowance received in parent U.S. Appl. No. 15/350,544 dated Mar. 21, 2019.

Communication dated Jun. 24, 2019, issued by the European Patent Office in counterpart European Application No. 17744506.1.

* cited by examiner

ELECTRONIC DEVICE AND CONTROL METHOD THEREOF

CROSS-REFERENCE TO RELATED APPLICATIONS

This application is a continuation of U.S. application Ser. No. 15/350,544 filed Nov. 14, 2016, which claims priority from Korean Patent Application No. 10-2016-0009382, filed on Jan. 26, 2016 in the Korean Intellectual Property Office, the disclosures of which are incorporated herein by reference in their entireties.

BACKGROUND

1. Field

Apparatuses and methods consistent with exemplary embodiments relate to an electronic device and a control method thereof, and more particularly, to an electronic device and a control method thereof, for measuring a sleeping state of a user in real time.

2. Description of the Related Art

In general, sleep may be classified into a sleeping stage and an awakening stage from a physiological point of view. The sleeping stage may be classified into rapid eye movement (REM) sleep and non-REM (NREM) sleep.

Polysomnography is a method for measuring sleep stages and requires various sensors which are attached to a head, a nose, a chest, an abdomen, etc. during sleep. The polysomnography is performed by an expert in a hospital. Accordingly, recently, devices for easily measuring sleep stages at home have been developed.

However, in related art devices, the sensors stay continuously activated during sleep, increasing battery consumption and, thus, when a battery is charged only once, the devices are not capable of being used for a long time. In addition, the device is driven using a post-processing method and, thus, a user is capable of checking a sleep result after a sleep stage detection algorithm is completely terminated. For example, the user needs to wait for about 30 minutes after user sleep is terminated in order to check the result.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide an electronic device and a control method thereof, for measuring a sleeping state in real time.

According to an aspect of an exemplary embodiment, an electronic device includes a first sensor configured to generate a movement signal according to a user movement, a second sensor configured to physically contact the user to generate a user bio-signal, a processor configured to determine a user sleeping state using the generated movement signal and the generated user bio-signal in each of time periods and to determine an operation state of another electronic device based on the determined sleeping state in respective time periods, and a communicator configured to transmit a control command corresponding to the determined operation state to the another electronic device.

The processor may determine the user sleeping state as any one of an awakening stage, an NREM sleeping stage, and a REM sleeping stage using the generated movement signal and the generated user bio-signal.

The processor may smooth a user bio-signal generated for one period using a user bio-signal generated prior to the one period and compare the smoothed user bio-signal with a certain value to determine a user sleeping state in the one period.

The electronic device may further include an input unit configured to receive a sleep analysis start command, wherein the processor may control the first sensor and the second sensor to generate a movement signal and a user bio-signal, respectively in response to the sleep analysis start command being received.

The input unit may receive a sleep analysis termination command, and the processor may calculate sleep efficiency from a time point in which the sleep analysis start command is received to a time point in which the sleep analysis termination command is received in response to the sleep analysis termination command being received.

The first sensor may include at least one among an acceleration sensor, a gyro sensor, and a gravity sensor, and the second sensor may be a heartbeat sensor configured to measure a heartbeat of the user.

The heartbeat sensor may be a sensor configured to emit light to generate a photoplethysmography (PPG) signal.

The processor may control the heartbeat sensor to periodically emit light.

The processor may control the communicator to transmit a control command corresponding to a changed operation state of another electronic device in response to the operation state being changed.

The electronic device may be a wearable device.

According to another aspect of an exemplary embodiment, a method of controlling an electronic device includes generating a movement signal according to a user movement through a first sensor of the electronic device, generating a user bio-signal through a second sensor of the electronic device that physically contacts the user, determining a user sleeping state using the generated movement signal and the generated user bio-signal in each of time periods, determining an operation state of another electronic device based on the determined sleeping state in respective time periods, and transmitting a control command corresponding to the determined operation state to the another electronic device.

The determining may include determining the user sleeping state as any one of an awakening stage, an NREM sleeping stage, and a REM sleeping stage using the generated movement signal and the generated user bio-signal.

The determining may include smoothing a user bio-signal generated for one period using a user bio-signal generated prior to the one period and comparing the smoothed user bio-signal with a certain value to determine a user sleeping state in the one period.

The method may further include receiving a sleep analysis start command, and controlling the first sensor and the second sensor to generate a movement signal and a user bio-signal, respectively in response to the sleep analysis start command being received.

The method may further include receiving a sleep analysis termination command, and calculating sleep efficiency from a time point in which the sleep analysis start command is received to a time point in which the sleep analysis termination command is received in response to the sleep analysis termination command being received.

The first sensor may include at least one among an acceleration sensor, a gyro sensor, and a gravity sensor, and the second sensor may be a heartbeat sensor configured to measure a heartbeat of the user.

The generating of the user bio-signal may include emitting light to generate a photoplethysmography (PPG) signal by the heartbeat sensor.

The generating of the user bio-signal may include periodically emitting light by the heartbeat sensor.

The transmitting may include transmitting a control command corresponding to a changed operation state of another electronic device in response to the operation state being changed.

According to another aspect of an exemplary embodiment, there is provided a computer-readable recording medium having recorded thereon a program a program which, when executed by a computer system, causes the computer system to execute a method of controlling an electronic device, the method including: generating a movement signal based on a user movement by a first sensor of the electronic device; generating a user bio-signal by a second sensor of the electronic device that physically contacts the user; determining a user sleeping state using the generated movement signal and the generated user bio-signal in each of time periods; determining an operation state of another electronic device based on the determined sleeping state in respective time periods; and transmitting a control command corresponding to the determined operation state to the another electronic device.

According to another aspect of an exemplary embodiment, there is provided an apparatus including: a first sensor configured to detect a user movement and generate a movement signal based on the detected user movement; a second sensor configured to generate a user bio-signal, by being brought into physical contact with the user; and a microprocessor configured to control a peripheral device in correspondence with a user sleeping state by determining the user sleeping state based on the generated movement signal and the generated user bio-signal in each of respective time periods into which a portion of a user sleeping time is split, and controlling an operating state of the peripheral device, in each of the respective time periods, based on the determined sleeping state by transmitting an operational command corresponding to the determined user sleeping state to the peripheral device, the operational command being a command for controlling a certain function of the peripheral device.

The first sensor includes at least one among an acceleration sensor, a gyro sensor, and a gravity sensor; and the second sensor includes a heartbeat measurement sensor.

The peripheral device includes at least one among a light source, a TV, a home temperature-controlling device, and a smartphone.

The apparatus further includes a display configured to display, on a screen, at least one among the user sleeping state and the operating state of the peripheral device determined for a certain time period.

The apparatus further includes a display, and the processor is configured to analyze the user sleeping state by receiving a sleep analysis start command for beginning a sleep analysis, at a first time point; acquiring, via the first sensor and the second sensor, the movement signal and the user bio-signal, respectively, based on the sleep analysis start command being received; receiving a sleep analysis termination command for ending the sleep analysis, at a second time point; and calculating a sleep efficiency of the user from the first time point to the second time point, and the display is configured to display the calculated sleep efficiency as at least one among a numeric value and a graph.

BRIEF DESCRIPTION OF THE DRAWINGS

The above and/or other aspects will become more apparent by describing certain exemplary embodiments, with reference to the accompanying drawings, in which.

DETAILED DESCRIPTION OF THE EXEMPLARY EMBODIMENTS

Figure 1:
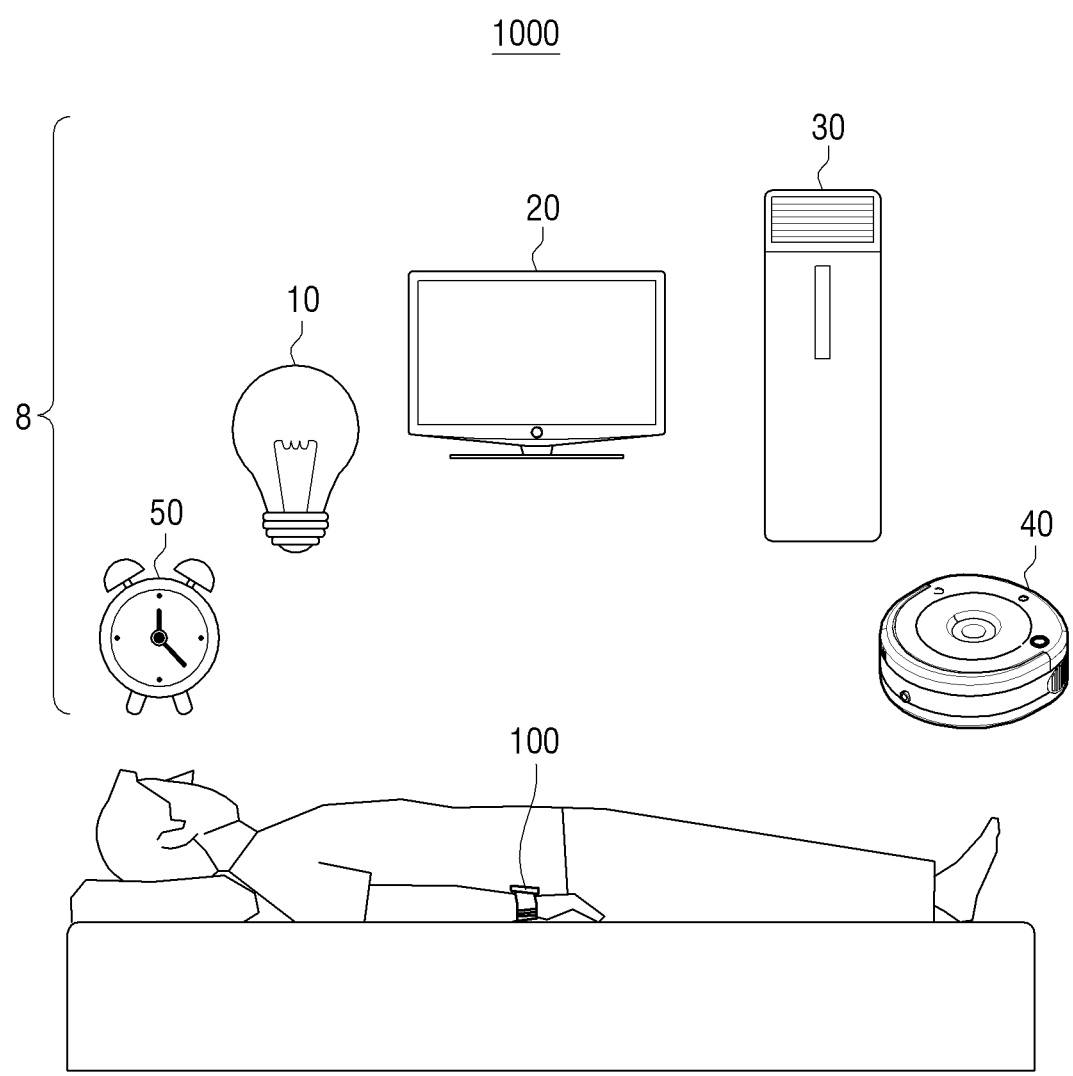
FIG. 1 is a diagram illustrating a sleep analysis system according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

It will be understood that, although the terms first, second, third etc. may be used herein to describe various elements, these elements should not be limited by these terms. These terms are only used to distinguish one element from another element.

The terminology used herein is for the purpose of describing particular embodiments only and is not intended to be limiting of the inventive concept. As used herein, the singular forms "a," "an" and "the" are intended to include the plural forms as well, unless the context clearly indicates otherwise. It will be further understood that the terms "comprises" or "comprising" when used in this specification, specify the presence of stated features, integers, steps, operations, elements, or components, but do not preclude the presence or addition of one or more other features, integers, steps, operations, elements, components, or groups thereof.

The terms, such as 'unit' should be understood as a unit that processes at least one function or operation and that may be embodied in a hardware manner, a software manner, or a combination of the hardware manner and the software manner. In addition, a plurality of 'units' may be integrated into at least one module to be embodied as at least one processor except for a 'unit' that needs to be embodied as a specific hardware.

FIG. 1 is a diagram illustrating a sleep analysis system 1000 according to an exemplary embodiment.

Referring to FIG. 1, the sleep analysis system 1000 may include an electronic device 100, i.e., a user device, and other electronic device or devices 8, i.e., peripheral devices, which may be controlled by the electronic device 100.

The electronic device 100 may analyze a user sleeping state in real time and control the other electronic devices 8 according to the sleeping state.

The electronic device 100 may be a device for analyzing a user sleeping state, such as a watch type device illustrated in FIG. 1 and may be embodied in various forms such as a patch, glasses, a hat, a headband, an earphone, and a headset. However, the electronic device 100 is not limited to a wearable device and may include a user device such as a smartphone.

The other electronic devices 8 may be devices that are operable according to control of the electronic device 100 and may be devices that are wirelessly communicable with the electronic device 100.

For example, the other electronic devices 8 may include at least one among a lighting device 10, a television (TV) 20, an air conditioner 30, a robot cleaner 40, an alarm clock 50, etc., which may change an operation state according to control of the electronic device 100.

In detail, the other electronic devices 8 may change an operation state according to a user sleeping state. For example, according to the user sleeping state, brightness of the lighting device 10 may be adjusted, the TV 20 may be powered off, a temperature of the air conditioner 30 or a heater may be adjusted, the robot cleaner 40 may be powered off or may be controlled not to enter a room without a user, and/or the alarm clock 50 may be controlled to make alarm sound at appropriate timing.

During control of the other electronic devices 8, the electronic device 100 may directly transmit a command or may transmit a command through a managing device that manages the other electronic devices 8. The managing device may be a home server, a smartphone, or the like and may be any one of the other electronic devices 8.

According to another exemplary embodiment, the other electronic devices 8 may request the electronic device 100 for information on a user sleeping state and may autonomously change an operation state according to the user sleeping state.

That is, when the electronic device 100 controls the other electronic devices 8, various methods may be used as described above. Accordingly, information transmitted to control the other electronic devices 8 by the electronic device 100 may include a command for directly changing operation states of the other electronic devices 8 or include information for autonomously changing operation states based on information received from the electronic device 100 by the other electronic devices 8.

The other electronic devices 8 illustrated in FIG. 1 are merely examples and, thus, devices controllable by the electronic device 100 are not limited thereto.

Figure 2:
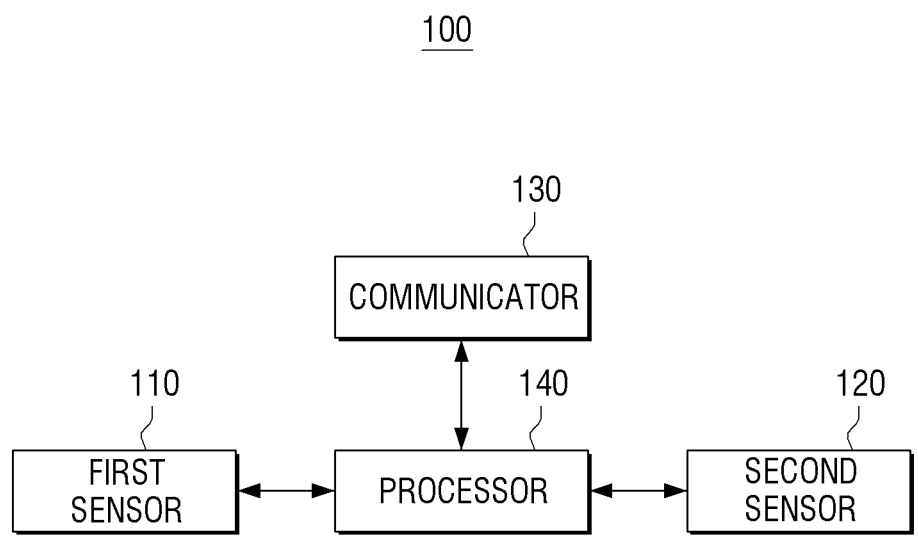
FIG. 2 is a block diagram of a structure of an electronic device according to an exemplary embodiment.

FIG. 2 is a block diagram of a structure of the electronic device 100 according to an exemplary embodiment.

Referring to FIG. 2, the electronic device 100 may include a first sensor 110, a second sensor 120, a communicator 130, and a processor 140.

The first sensor 110 may generate a movement signal according to a user movement. When the electronic device 100 is a wearable device, the first sensor 110 may generate a movement signal according to the movement of the user who wears the electronic device 100. The electronic device 100 may be disposed above or below an object (e.g., mattress) on which a user lies and the first sensor 110 may generate a movement signal according to movement of an object corresponding to the user movement.

The first sensor 110 may include at least one of, for example, a gyro sensor, a terrestrial magnetism sensor, an acceleration sensor, and a pressure sensor.

The acceleration sensor may sense an inclination degree using gravity. That is, when a gravity value is 1 g in the case of sensing in a vertical direction, if an inclination degree has a value less than 1 g when a corresponding object is obliquely inclined and if an inclination degree has a value of −1 g when the object is stood upside down. The acceleration sensor may output a pitch angle and a roll angle using such a principle. The acceleration sensor may be a 2-axis or 3-axis fluxgate sensor.

The terrestrial magnetism sensor is a device for measuring the intensity and direction of terrestrial magnetism. In particular, a terrestrial magnetism sensor using fluxgate may be a fluxgate-type terrestrial magnetism sensor. The terrestrial magnetism sensor may be a 2-axis or 3-axis fluxgate sensor as the acceleration sensor.

The gyro sensor may sense angular speed and sense an inclination degree based on a rotation axis using Coriolis force. The gyro sensor may use both a mechanical sensor and an electronic sensor.

The pressure sensor may include at least one among a piezoelectric pressure sensor, a strain gauge pressure sensor, a capacitive pressure sensor, or the like. The piezoelectric pressure sensor may calculate a pressure value according to a voltage value using a piezoelectric material. The strain gauge pressure sensor may calculate a pressure value according to a resistance value of a strain gauge using the strain gauge, the resistance value of which varies in response to tensile force or compressive force. The strain gauge may include a wire or a spring. The capacitive pressure sensor may detect a capacity change according to a distance between electrodes, which is changed in response to an applied pressure, using two electrodes to calculate a pressure value.

The electronic device 100 may generate a movement signal according to a user movement while being spaced apart from the user. The first sensor 110 may be a device for generating a movement signal according to the user movement based on an image captured by the user. For example, various multiple sensor and/or devices for generating a movement signal according to a user movement may be embodied as the first sensor 110.

The second sensor 120 may contact the user to generate a user bio-signal.

In detail, the second sensor 120 may be a device for generating a user bio-signal such as a photoplethysmography (PPG) signal, an electrocardiogram (ECG) signal, a blood volume pulse (BVP) signal, a heart rate variability (HRV) signal, an electroencephalography (EEG) signal, an electromyography (EMG) signal, or an electrooculography (EOG) signal.

For example, the case in which the second sensor 120 is a device for generating a photoplethysmography (PPG) signal is described below in more detail with reference to FIG. 3.

Figure 3:
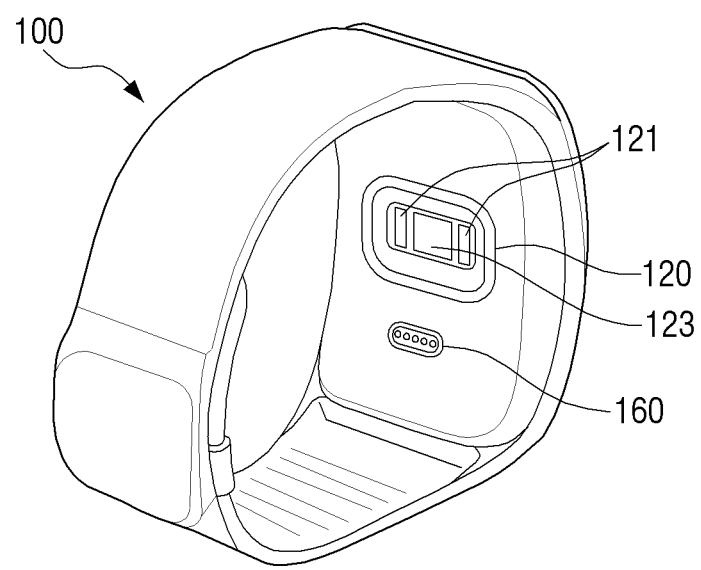
FIGS. 3 and 4 are diagrams illustrating an electronic device according to an exemplary embodiment.

FIG. 3 is a diagram illustrating the electronic device 100 according to an exemplary embodiment. Referring to FIG. 3, the electronic device 100 may be shaped like a watch and may include the second sensor 120 disposed on a portion that a user body contacts.

The second sensor 120 may include a light emitter 121 and a light receiver 123.

The light emitter 121 may be a component for emitting light to a user. The light emitter 121 may be a light emitting diode (LED) or laser diode.

The light emitter 121 may include a plurality of LEDs for emitting light with different wavelengths. For example, the light emitter 121 may include a first LED for emitting light with a first wavelength and a second LED for emitting light with a second wavelength that is different from the first wavelength.

The light receiver 123 may receive light. The received light may be photoelectrically-converted to generate a current signal. The light receiver 123 may be a photodiode.

As illustrated in FIG. 3, when the light emitter 121 and the light receiver 123 are disposed on a same side, the light receiver 123 may receive light that is emitted by the light emitter 121 and reflected from the user. However, the arrangement of the light emitter 121 and the light receiver 123 is not limited to FIG. 3 and, thus, the light emitter 121 and the light receiver 123 may be arranged to face each other across a part of a user body (e.g., a wrist and a finger). The light receiver 123 may receive light that is emitted from the light emitter 121 and passes through the user.

The processor 140 may analyze contraction and relaxation degrees of a blood vessel of a user based on the amount of received light to measure a heartbeat of the user and calculate a heart rate based on the heartbeat of the user.

When the second sensor 120 is a sensor for measuring a heartbeat, the second sensor 120 may be a heartbeat sensor.

As described above, when light is emitted to measure a heartbeat, the processor 140 may control the second sensor 120 to intermittently emit light.

For example, when one period for determining one sleeping state is 30 seconds, the processor 140 may control the second sensor 120 to emit light only for six seconds of the 30 seconds and not to emit light for the remaining 24 seconds. The processor 140 may calculate an average heart rate based on a heartbeat for six seconds and determine the calculated average heart rate as a heart rate of one period.

Light may be intermittently emitted rather than being continuously emitted to reduce power consumption.

The electronic device 100 may charge a battery through a charging terminal 160 and the processor 140 may control the second sensor 120 to adjust time for emitting light according to a battery charging state of the electronic device 100.

For example, when a battery charging amount is greater than or equal to a preset amount, the processor 140 may control the second sensor 120 to continuously emit light. When a battery charging amount is less than a preset amount, the processor 140 may control the second sensor 120 to intermittently emit and to reduce time for emitting light as a battery charging amount is reduced.

The user may manually set time for emitting light.

The communicator 130, e.g., a transceiver or a communication interface, may be a component for communication with various other electronic devices. The communicator 130 may perform communication using various communication methods such as near field communication (NFC), wireless LAN, infrared (IR) communication, ZigBee communication, Wi-Fi, and Bluetooth. Other electronic devices may be home appliances such as a light device, a TV, and an air conditioner or a smartphone, as described with reference to FIG. 1.

The communicator 130 may transmit a control command corresponding to an operation state that is determined based on a user sleeping state to another electronic device 8. The communicator 130 may transmit a sleep analysis result to another electronic device 8. The communicator 130 may receive state information from another electronic device 8.

The processor 140 may be a component for controlling an overall operation of the electronic device 100.

For example, the processor 140 may include a microprocessor, a central processing unit (CPU), a rapid access memory (RAM), a read only memory (ROM), and a system bus. The ROM may store a command set for system booting and the CPU may copy an operating system (OS) stored in a storage of the electronic device 100 according to a command stored in the ROM and execute the OS to boot a system. When booting is completed, the CPU may copy various applications stored in the storage to an RAM, execute the applications, and perform various operations. For example, the processor 140 may include one CPU or a plurality of CPUs (DSP, SoC, etc.).

The processor 140 may determine a user sleeping state using a movement signal and a user bio-signal that are generated for a preset period. For example, when a preset period is 30 seconds, an operation of determining a sleeping state is every 30 seconds.

The processor 140 may determine a user sleeping state as any one of three-stage sleeping state. The three-stage sleeping state may include a first sleeping state, a second sleeping state, and a third sleeping state.

The first sleeping state, the second sleeping state, and the third sleeping state may correspond to a sleep state that becomes deeper. For example, the first sleeping state, the second sleeping state, and the third sleeping state may be "awakening stage, REM sleeping stage, and deep sleeping stage", "awakening stage, REM sleeping stage, and NREM sleeping stage", "slight sleeping stage, REM sleeping stage, and NREM sleeping stage", or "slight sleeping stage, REM sleeping stage, and deep sleeping stage".

The processor 140 may determine that a current sleeping state is a first sleeping state based on a movement signal generated by the first sensor 110. For example, when movement intensity measured based on a movement signal at a specific period is greater than or equal to a preset degree, the current sleeping state may be determined as the first sleeping state. That is, when movement is high, the current sleeping state may be determined as awakening or a slight sleeping state.

The processor 140 may smooth a movement signal generated for one period using the movement signal generated prior to the one period and compare the smoothed user bio-signal with a preset value to determine a user sleeping state in the one period.

The processor 140 may determine what the current sleeping state is the based on the user bio-signal generated by the second sensor 120. For example, when a heart rate that is measured based on a user bio-signal in a specific period is greater than or equal to a preset value, the current sleeping state may be determined as the second sleeping state.

The processor 140 may smooth a user bio-signal generated for one period using a user bio-signal generated prior to the one period and compare the smoothed user bio-signal with a preset value to verify a user sleeping state in the one period.

Upon verifying that the current sleeping state is the first sleeping state in a specific period, the processor 140 may determine that the corresponding period is the first sleeping state irrespective of the prior determination of the current sleeping state as the second sleeping state. In other words, when the first sleeping state and the second sleeping state are simultaneously determined in a specific period, determination as the second sleeping state may be disregarded and the current sleeping state may be determined as the first sleeping state. That is, the processor 140 may determine a sleeping state by first considering a user movement.

Accordingly, the processor 140 may perform both an operation of determining the first sleeping state and an operation of determining the second sleeping state. Alternatively, the processor 140 may perform the operation of determining the first sleeping state to determine the current sleeping state as the first sleeping state, and does not further perform the operation of determining the second sleeping state, in order to reduce memory consumption for sleeping state analysis processing.

Upon determining the current sleeping state is not the first sleeping state or the second sleeping state in a specific period as the aforementioned analysis result, the processor 140 may determine that a specific period is the third sleeping state.

Upon determining a sleeping state, the processor 140 may determine operation states of another electronic device 8 based on the determined sleeping state.

The case in which another electronic device 8 is a robot cleaner is described below as an example. Upon determining that a sleeping state in a specific period is determined as the first sleeping state or the second sleeping state, the processor 140 may determine an operation state of the robot cleaner 40 as a power off state. When the sleeping state is determined as the third sleeping state, the operation state of the robot cleaner 40 may be determined as a power on state. That is, the robot cleaner 40 is not operated in a slight sleeping state and since the sleeping user is insensitive in a deep sleeping state, the robot cleaner 40 may be operated in the deep sleeping state.

As described above, the processor 140 may determine an operation state of another electronic device 8 and control the communicator 130 to transmit a control command corresponding to the determined operation state to another electronic device 8.

The control command may be transmitted every period in response to the operation state that is determined every period.

According to another exemplary embodiment, the control command may be transmitted only when an operation state is to be changed rather than being transmitted every period. In detail, when an operation state of another electronic device 8 is determined to be changed, the processor 140 may control the communicator 130 to transmit a control command corresponding to the changed operation state.

For example, upon determining an operation state of a robot cleaner 40 as another electronic device 8 as a power off state in a first period, the processor 140 may transmit a control command corresponding to the power off state and, then, if it is determined that the operation state of the robot cleaner 40 is a power off state in a second period, the processor 140 does not transmit a control command corresponding to the power off state of the second period to the robot cleaner 40. Upon determining the operation state of a robot cleaner 40 in a third period as a power on state, the processor 140 may detect that the operation state is changed and transmit a control command corresponding to a power on state to the robot cleaner 40.

The electronic device 100 may receive selection of sleeping analysis start, sleeping analysis termination, a device as a control target, and so on according to a user input through an input unit.

Figure 4:
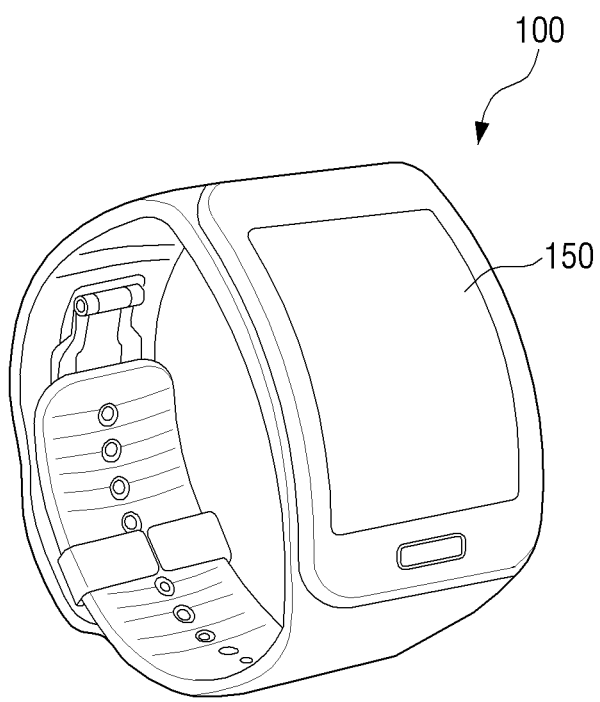

FIG. 4 is a diagram showing an input unit 150 of the electronic device 100 according to an exemplary embodiment.

The input unit 150 may be a component for receiving a user command and may include a touchscreen as illustrated in FIG. 4. A touchscreen may be a device for performing a display function and receiving a user input. However, exemplary embodiments are not limited thereto and the input unit 150 may include a physical button, or other appropriate input means.

Upon receiving a sleep analysis start command, the processor 140 may control the first sensor 110 and the second sensor 120 to generate a movement signal and a user bio-signal, respectively. For example, the sleep analysis start command may be generated based on the user input provided through input unit 150 to specify a period of time during which the sleep analysis is to be performed or to specify when the sleep analysis is to be started. However, this is not limiting.

After receiving the sleep analysis start command, the processor 140 may determine a sleeping state of a user every preset period and determine an operation state of another electronic device 8 based on the sleeping state determined every preset period, as described above.

Upon receiving a sleep analysis termination command, the processor 140 may calculate sleep efficiency starting from a time point at which the sleep analysis start command is received to a time point at which a sleep analysis termination command is received. The sleep analysis termination command may be generated based on the user input provided through the input unit 150. For example, the sleep analysis termination command may be generated based on the input by the user to specify a period of time during which the sleep analysis is to be performed or to specify when the sleep analysis is to be terminated. However, this is not limiting.

The sleep efficiency refers to an index indicating a degree by which a user tosses and turns for a sleep period. Accordingly, the processor 140 may calculate sleep efficiency based on the movement signal generated by the first sensor 110 during a sleep period. The calculation result may be displayed on, for example, a display of the electronic device 100.

After receiving the sleep analysis start command, the processor 140 may determine an operation state of another electronic device 8 based on the sleeping state determined every preset period, as described above. The another electronic device 8 may be pre-selected by a user. According to an exemplary embodiment, the user may be provided with a UI for selecting a device to be controlled during sleep. However, this is not limiting and the user may be provided with menus, icons or images showing the various devices, etc.

The processor 140 may provide a control target device selection UI to the user through a display (e.g., a touchscreen of FIG. 4) of the electronic device 100, which is described below with reference to FIG. 5.

Figure 5:
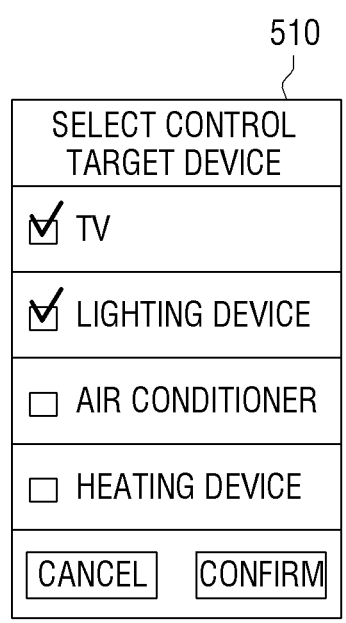
FIG. 5 is a diagram illustrating a control target device selection user interface (UI) according to an exemplary embodiment.

FIG. 5 is a diagram illustrating a control target device selection UI 510 according to an exemplary embodiment.

A user may select a device to be controlled during sleep through the control target device selection UI 510. The control target device selection UI 510 may be displayed on, for example, a touchscreen of the electronic device 100.

As illustrated in FIG. 5, when 'TV' and 'lighting device' are selected, the processor 140 may control the communicator 130 to transmit a control command corresponding to the determined sleeping state to a TV 20 and a lighting device 10. However, this is not limiting and the electronic device 100 may automatically select and control various peripheral devices based on the detected sleeping state of the user, current environmental conditions, etc.

In the above example, although the case in which the electronic device 100 directly controls another electronic device 8 and a user command such as a sleep analysis start command is input directly to the electronic device 100 has been described, the aforementioned function may be performed by another user device instead of the electronic device 100.

The another user device may be another user terminal device, as described below in more detail with reference to FIG. 6.

Figure 6:
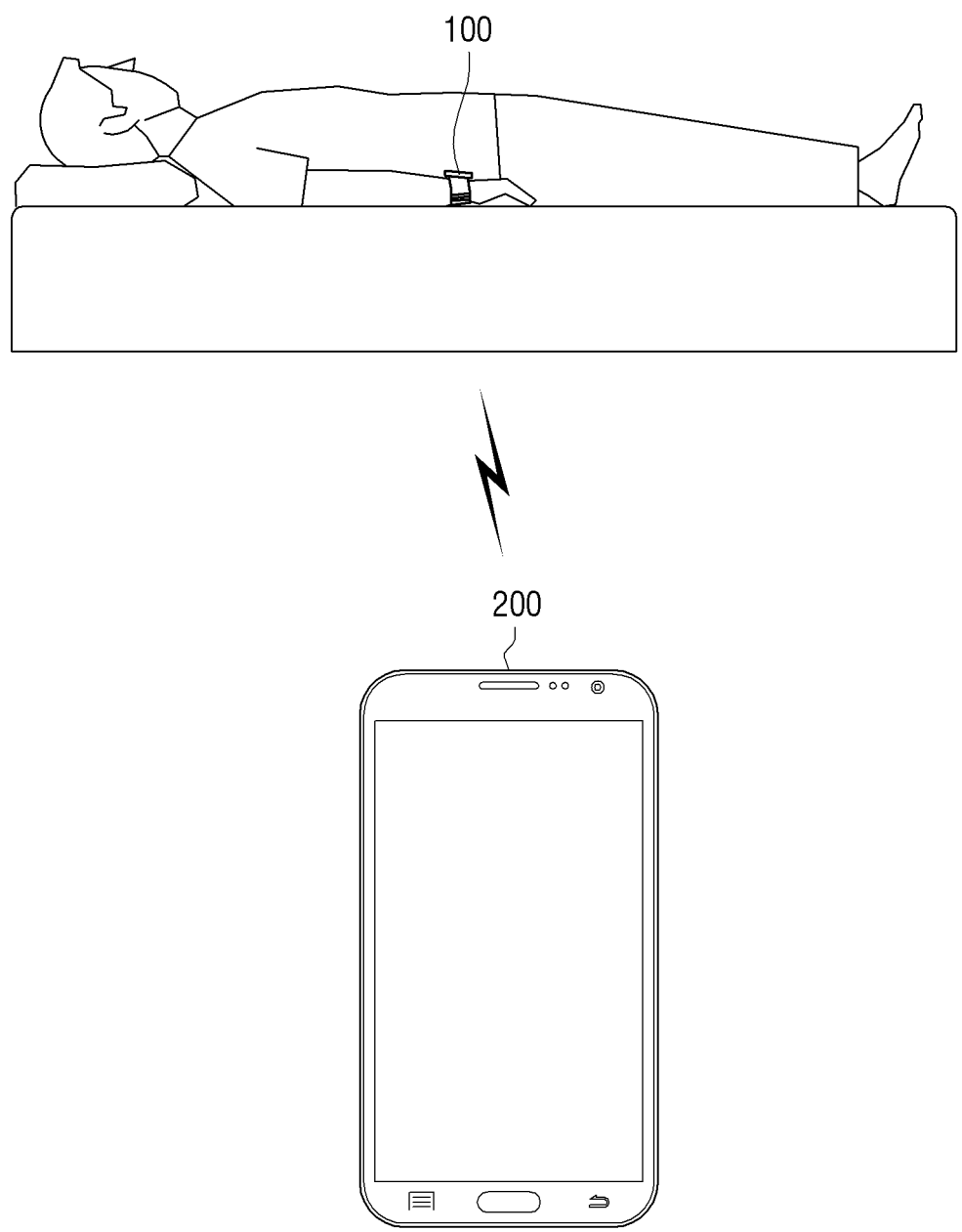
FIG. 6 is a diagram of an interaction between an electronic device and another user terminal device according to an exemplary embodiment.

FIG. 6 is a diagram of an interaction between the electronic device 100 and another user terminal device 200 according to an exemplary embodiment.

Referring to FIG. 6, the electronic device 100 may communicate with the user terminal device 200 via wireless or wired communication. For example, the electronic device 100 may be connected to the user terminal device 200 via Bluetooth.

The electronic device 100 may perform an operation of generating the movement signal and the user bio-signal through the first sensor 110 and the second sensor 120 and determination of a user sleeping state may be performed by the user terminal device 200 that receives the generated signals. In addition, decision of an operation state of another electronic device 8 according to a user sleeping state and transmission of a control command corresponding to the operation state may be performed by the user terminal device 200.

Alternatively, the electronic device 100 may perform determination of a user sleeping state and the user terminal device 200 may perform the transmission of a control command corresponding to the operation state.

A user command such as a sleep analysis start command and a sleep termination start command may be input from the user terminal device 200 instead of the electronic device 100 and transmitted to the electronic device 100, the control target device selection UI 510 described with reference to FIG. 5 may be displayed on the user terminal device 200, and management of a control target device may be performed by the user terminal device 200. The calculated sleep efficiency may be displayed on the user terminal device 200. For example, the calculated sleep efficiency may be displayed as a numerical value or a graph, in relation to time.

According to the exemplary embodiment, when the electronic device 100 is a small size wearable device and has a lower capacity memory, processing that requires a higher memory consumption may be performed by the user terminal device 200 instead of the electronic device 100. When the electronic device 100 is a device that does not include a display and an input unit, a user may view various information items and receive various user commands through the user terminal device 200 including a display and an input unit. When the electronic device 100 supports only short-range wireless communication such as Bluetooth, it may be impossible to directly control another faraway electronic device. Accordingly, the user terminal device 200 for supporting long-range wireless communication such as Wi-Fi as well as short-range wireless communication such as Bluetooth may control another faraway electronic device based on information (e.g., a movement signal and a user bio-signal) received from the electronic device 100.

Figure 7:
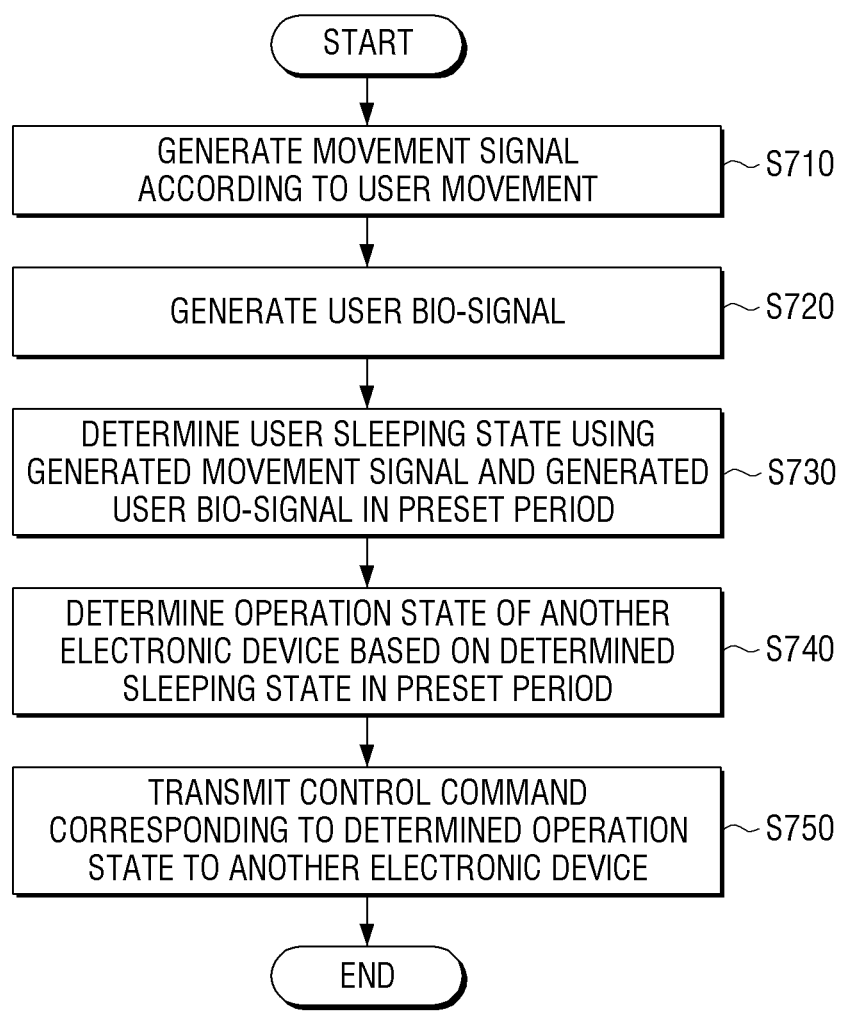
FIG. 7 is a flowchart of a method of controlling an electronic device according to an exemplary embodiment.

FIG. 7 is a flowchart of a method of controlling an electronic device according to an exemplary embodiment.

Referring to FIG. 7, a movement signal according to a user movement may be generated through the first sensor 110 of the electronic device 100 (operation S710).

A user bio-signal may be generated through the second sensor 120 of the electronic device 100 that contacts a user (operation S720).

The first sensor 110 and the second sensor 120 may be set to continuously generate the movement signal and the user bio-signal. Alternatively, the first sensor 110 and the second sensor 120 may be set to generate the signals only at a predetermined time point. For example, the user may pre-set a time period (e.g., from 11 pm to 7 am) in which the user mainly sleeps as sleep analysis time in the electronic device 100. The signals may be generated from when the user inputs a sleep analysis start command and until the user inputs a sleep analysis termination command. When the sleep analysis start command is input and, then, it is determined that the user is completely awaken through movement analysis through the first sensor 110, sleep analysis may be terminated.

A user sleeping state may be determined using the generated movement signal and the generated user bio-signal every preset period (operation S730).

An operation state of another electronic device 8 may be determined based on the determined sleeping state every preset period (operation S740).

The another electronic device 8 may be a device pre-registered in the electronic device 100. The operation state according to the determined sleeping state may be different according to respective electronic devices.

For example, when another electronic device 8 is a smartphone, if a current sleeping state is determined to be a REM sleeping stage or a NREM sleeping stage, the current operation state may be determined to be a mute state.

As another example, when another electronic device 8 is a heating device, the electronic device 100 may determine an operation state of the heating device as a temperature state appropriate for an awakening stage, a REM sleeping stage, or a NREM sleeping stage.

As another example, when another electronic device 8 is an audio device, an operation state of the audio device may be determined based on the sleep duration time and sleeping state of the electronic device 100. When user wake-up is determined to be imminent based on sleep duration time so far and a current sleeping state, the electronic device 100 may determine an operation state of the audio device as a preset music on-state. The preset music may be preset as dulcet music by the user. As another example, when another electronic device 8 is an electric rice cooker or a coffee machine, upon determining that user wake-up is imminent, the electronic device 100 may determine an operation state of the electric rice cooker or the coffee machine as an on-state.

As another example, when another electronic device 8 is a security device, upon determining that a sleeping state is a REM sleeping stage or a NREM sleeping stage, the electronic device 100 may determine the security device in an on-state.

The electronic device 100 may transmit a control command corresponding to the determined operation state to another electronic device 8 (operation S750).

The electronic device 100 may perform control to transmit the control command corresponding to the operation state determined every period to another electronic device 8 every period or to transmit the control command only when an operation state is to be changed from the previously set operation state.

Another electronic device 8 that receives the control command may change the operation state according to the control command.

For example, in the case of a TV 20, when a control command corresponding to an operation state of power-off is received, power may be off. When power is already off, a power-off state may be maintained without changes.

The electronic device 100 may determine whether the control command is transmitted, based on a distance with another electronic device 8. In detail, the electronic device 100 may determine the distance with another electronic device 8 using received signal strength indication (RSSI) from another electronic device 8. The electronic device 100 may transmit the control command only when the distance with another electronic device 8 is less than a preset distance. For example, when another electronic device 8 is a TV 20, if a distance between the TV 20 and a user who wears the electronic device 100 is greater than or equal to a preset distance, the user is not affected by noise of the TV 20 and, thus, it may not be necessary to power off the TV 20. In addition, other family members may view a TV 20 in a living room while the user of the electronic device 100 sleeps and, in this case, the TV 20 does not have to be automatically powered off.

As such, whether a control command for controlling another electronic device 8 is transmitted may be determined according to a situation and the characteristics of another electronic device 8. Alternatively, even if receiving the control command, another electronic device 8 may be operated to disregard the control command according to a situation and the characteristics of another electronic device 8, as described above.

According to another exemplary embodiment, the electronic device 100 may request another preset electronic device to transmit state information and receive the state information from other electronic devices. The electronic device 100 may recognize current operation states of other electronic devices based on the received state information and transmit the control command to other electronic devices only when an operation state needs to be changed according to a user sleeping state. For example, upon recognizing that a TV 20 is in an off-state based on state information received from the TV 20, the electronic device 100 may not transmit a control command for powering off the TV 20 according to the user sleeping state.

According to exemplary embodiments, operation states of electronic devices may be controlled in real time according to a user sleeping state and, thus, user convenience may be further improved.

Figure 8:
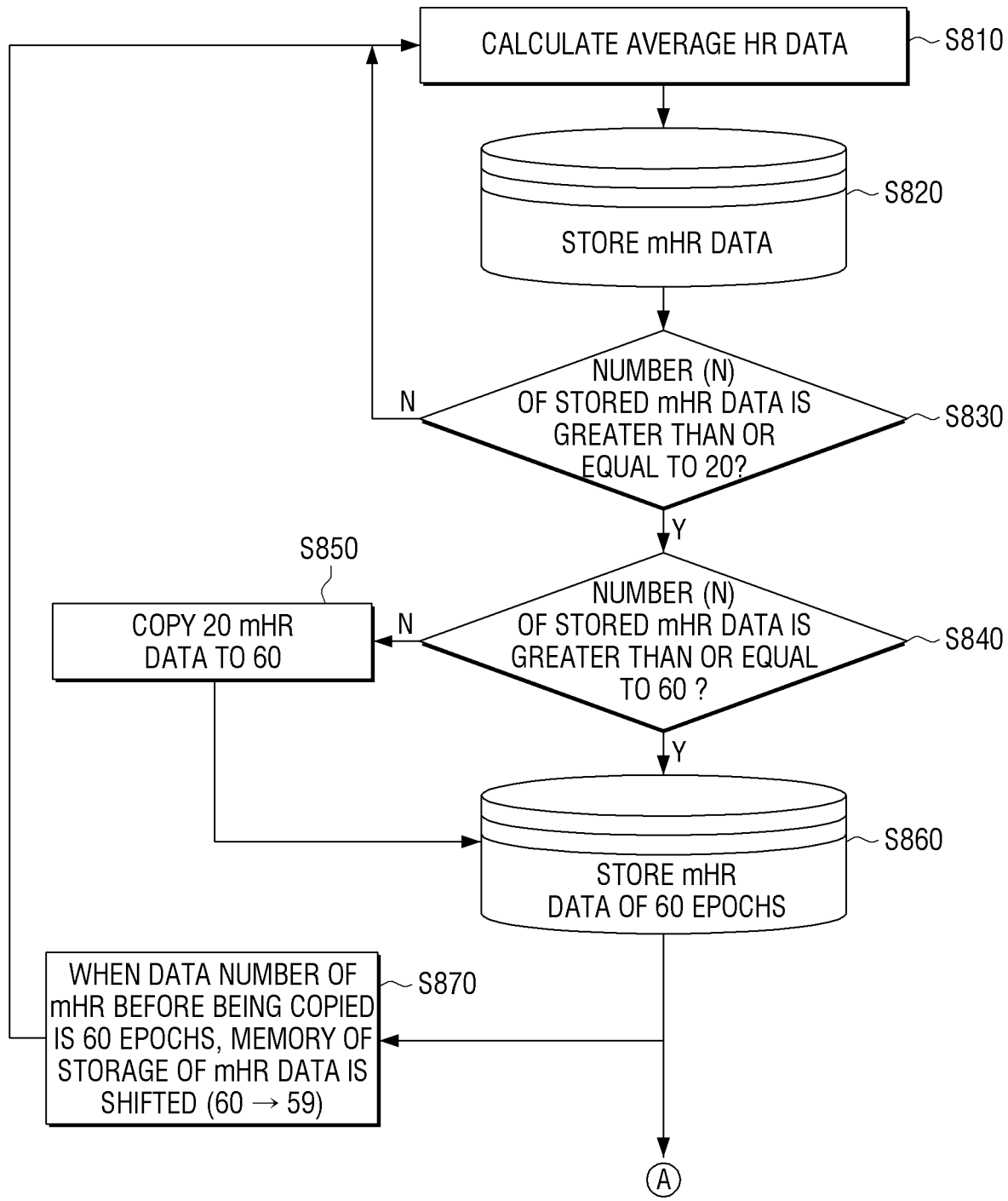
FIGS. 8, 9, and 10 are flowcharts of a method of determining whether a current sleeping stage is a REM sleeping stage or an NREM sleeping stage of an electronic device according to an exemplary embodiment.
Figure 9:
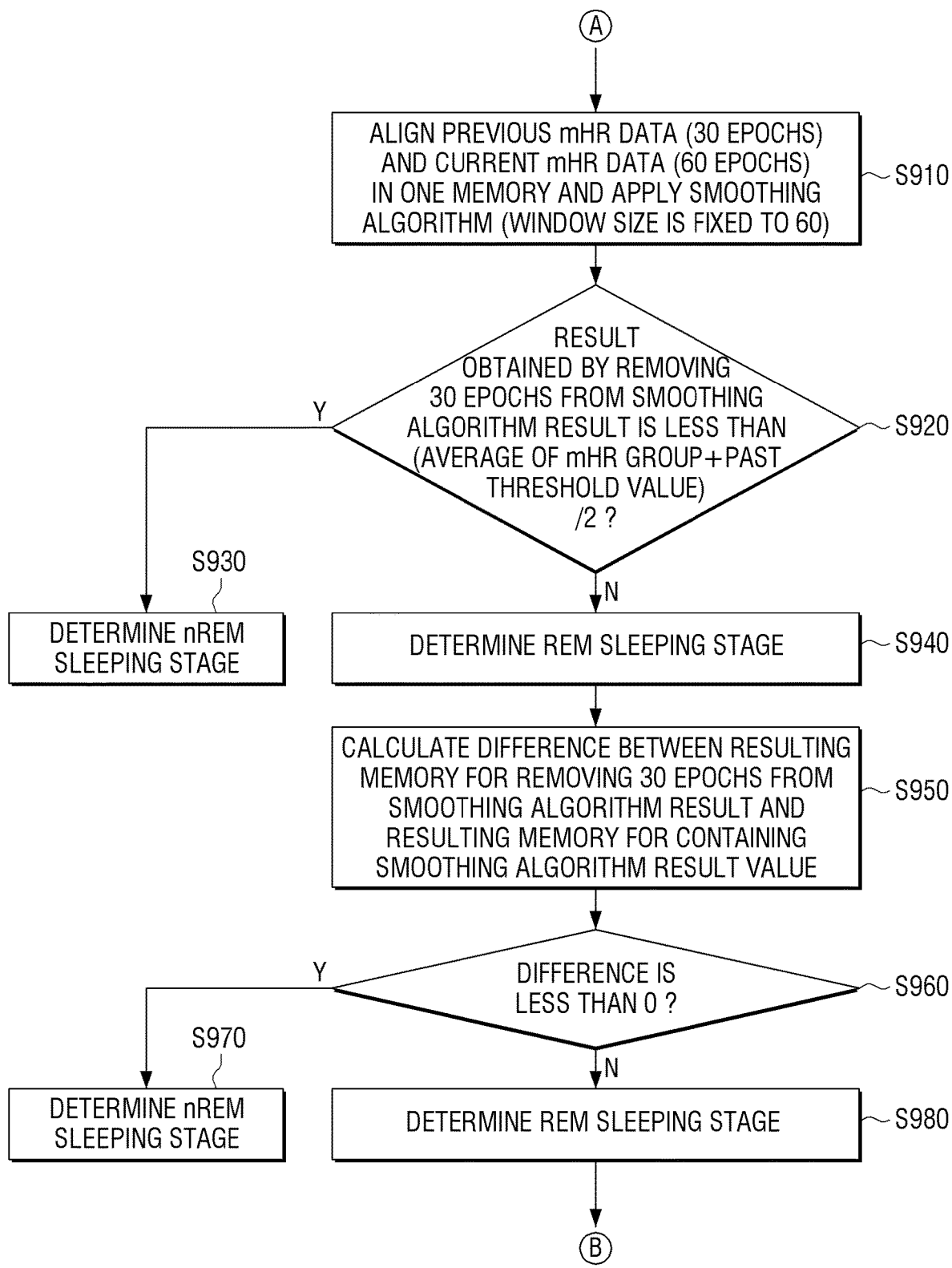
Figure 10:
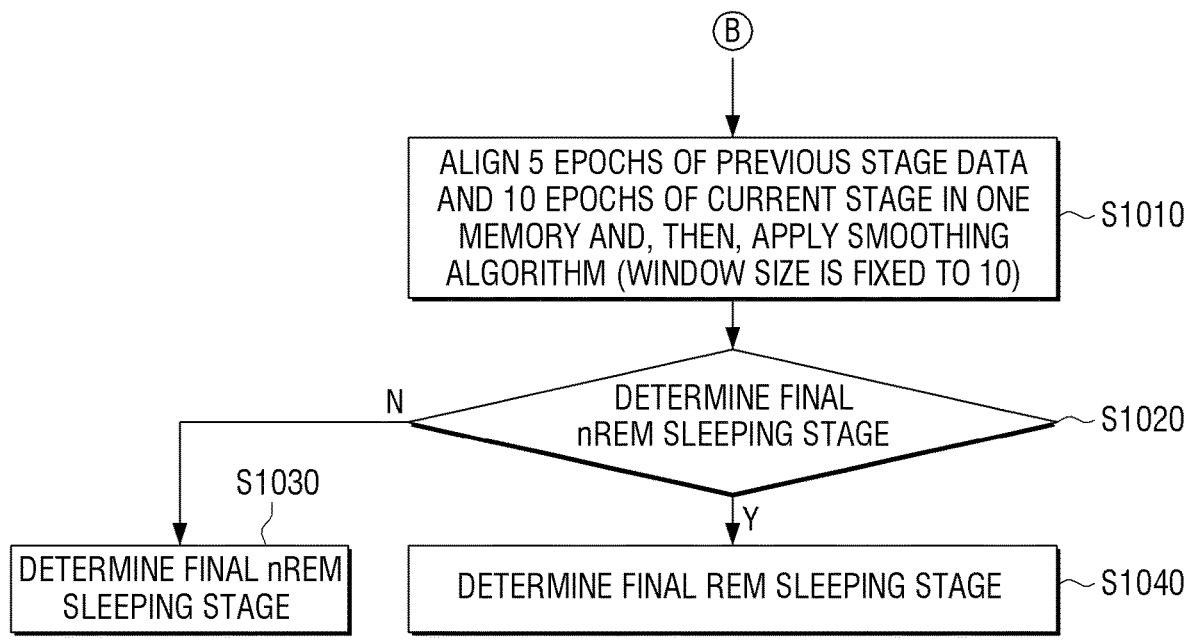

FIGS. 8 to 10 are flowcharts of a method of determining whether the current sleeping stage is a REM sleeping stage or a NREM sleeping stage of the electronic device 100 according to an exemplary embodiment.

FIG. 8 is a flowchart of extraction and collection of average HR data (average heart rate data).

Referring to FIG. 8, first, the processor 140 may collect calculated average HR data from an ECG sensor or a PPG sensor (operation S810). In this case, average (mean) HR (mHR) of an HR data group for six seconds may be calculated in a period of 30 seconds (1 epoch). However, this is not limiting.

The processor 140 may store the collected mHR data in a storage for collecting mHR data (operation S820).

The processor 140 may determine whether the number (n) of the stored mHR data is greater than or equal to 20 (operation S830). This may be based on the case in which the number of at least required mHR data for feature extraction is preset to 20. However, this is not limiting.

When the number (n) of the stored mHR data is less than 20 (operation S830, N), the average HR data may be continuously collected.

When the number (n) of the stored mHR data is greater than or equal to 20 (operation S830, Y), the processor 140 may determine whether the number (n) of the stored mHR data is greater than or equal to 60 (operation S840). This may be based on the case in which the number of mHR data for calculating is preset to 60. However, this is not limiting.

When the number (n) of the stored mHR data is less than 60 (operation S840, N), 20 mHR data may be copied to 60 (operation S850).

When the number (n) of the stored mHR data is greater than or equal to 60 (operation S840, Y), the mHR data may be stored in a storage of mHR data of 60 epochs (operation S860).

When the number of mHR data before being copied is 60 epochs, a memory of the storage of the mHR data may be shifted to 59 from 60 (operation S870). However, this is not limiting.

FIG. 9 is a flowchart of feature detection and stage estimation.

Referring to FIG. 9, previous mHR data (30 epochs) and current mHR data (60 epochs) may be aligned in one memory and a smoothing algorithm may be applied (window size is fixed to 60) (operation S910). This is because slight change or discontinuity that adversely affects data is present due to noise and, thus, such change or discontinuity needs to be weakened or removed. This operation may be processing in a frequency domain and, thus, a high frequency component may be removed by a low pass filter. However, this is not limiting.

The processor 140 may determine whether a result obtained by removing 30 epochs from the smoothing algorithm result is less than a value obtained by dividing 'average of mHR group+past threshold value' by 2 (operation S920). However, this is not limiting. The operation S920 may be a primary comparing and separating operation.

When the result obtained by removing 30 epochs from the smoothing algorithm result is less than a value obtained by dividing 'average of mHR group+past threshold value' by 2 (operation S920, Y), an NREM sleeping stage may be determined (operation S930). When the result obtained by removing 30 epochs from the smoothing algorithm result is not less than a value obtained by dividing 'average of mHR group+past threshold value' by 2 (operation S920, N), a REM sleeping stage may be determined (operation S940).

The processor 140 may calculate a difference between a resulting memory for removing 30 epochs from the smoothing algorithm result and a resulting memory for containing the smoothing algorithm result value (operation S950). The memory for removing 30 epochs from the smoothing algorithm result may be pS_MeanHR[i] and the resulting memory for containing the smoothing algorithm result value may be pSS_MeanHR[i]. That is, pDiff_S_MeanHR[i]=pS_MeanHR[i]−pSS_MeanHR[i].

The processor 140 may determine whether the difference between the memory for removing 30 epochs from the smoothing algorithm result and the resulting memory for containing the smoothing algorithm result value is less than 0 (operation S960). However, this is not limiting. The operation S960 may be a secondary comparing and separating operation.

When the difference between the memory for removing 30 epochs from the smoothing algorithm result and the resulting memory for containing the smoothing algorithm result value is less than 0 (operation S960, Y), a NREM sleeping stage may be determined (operation S970). When the difference between the memory for removing 30 epochs from the smoothing algorithm result and the resulting memory for containing the smoothing algorithm result value is not less than 0 (operation S960, N), a REM sleeping stage may be confirmed (operation S980).

FIG. 10 is a flowchart of estimated stage correction and final result deduction.

Referring to FIG. 10, the processor 140 may align 5 epochs of a previous stage data and 10 epochs of a current stage in one memory and, then, apply the smoothing algorithm (a window size is fixed to 10) (operation S1010). Here, only 5 epochs of the result of 10 epochs may be applied to the result. However, this is not limiting. The REM sleep has continuity and, thus, only a specific level period after smoothing may be used.

The processor 140 may determine whether a current level is less than a wake level (operation S1020). In this case, a memory of first 5 epochs may be discarded from a REM stage memory (10 epochs of REM stage memory). However, this is not limiting.

When the current level is not less than the wake level, the current state may be finally determined as a NREM sleeping stage (operation S1030) and when the current level is less than the wake level, the current state may be finally determined as REM sleeping stage (operation S1040). Here, first 5 epochs of 10 epochs in the REM sleeping stage may be determined as a true value and a stage value of the fifth epoch may return to result data. However, this is not limiting.

Figure 11:
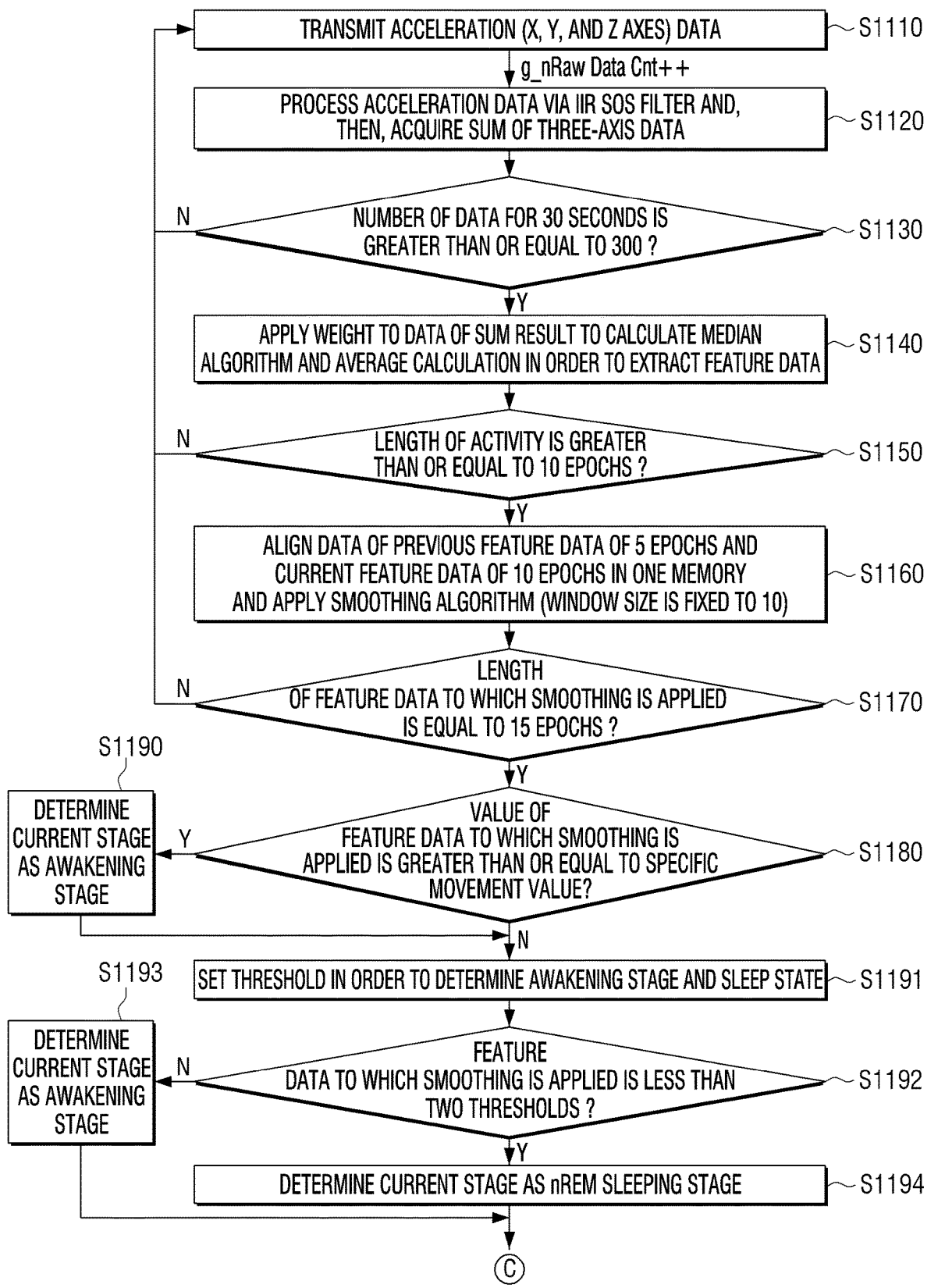
FIGS. 11 and 12 are flowcharts of a method of determining an awakening stage of an electronic device according to an exemplary embodiment.
Figure 12:
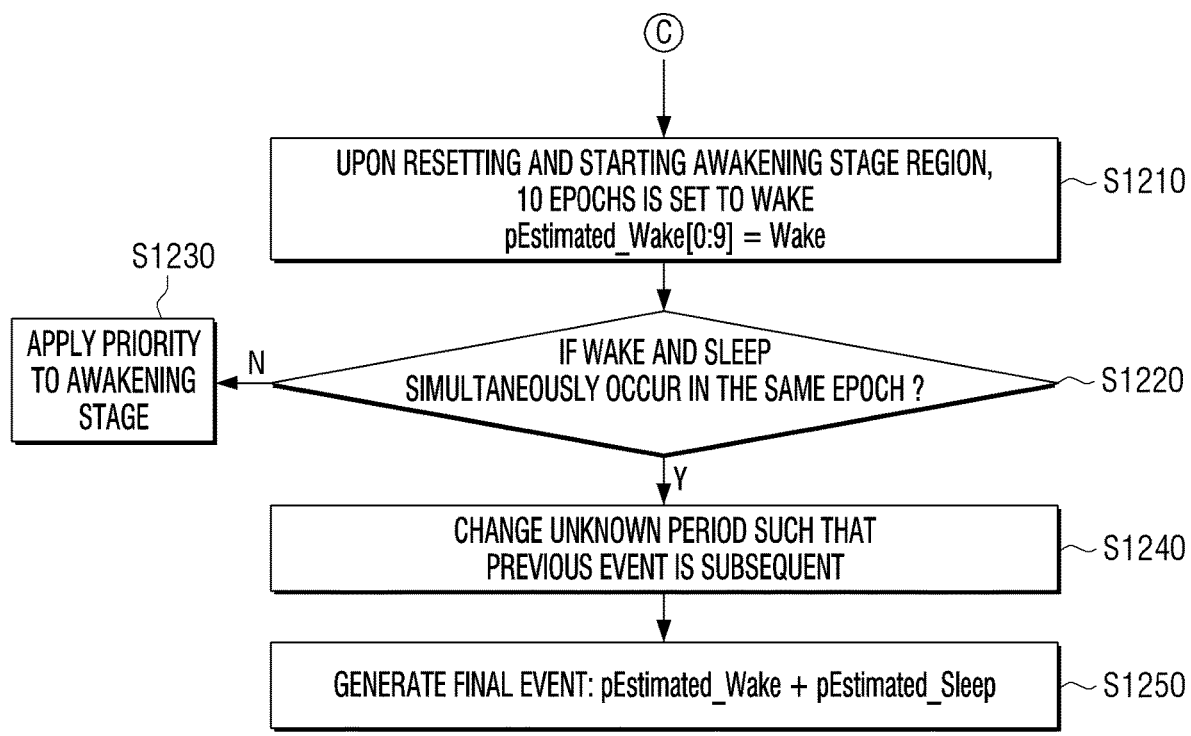

FIGS. 11 and 12 are flowcharts of a method of determining an awakening stage of the electronic device 100.

FIG. 11 is a flowchart of acceleration data collection, feature data extraction, and stage estimation.

Referring to FIG. 11, acceleration (X, Y, and Z axes) data may be transmitted at a period of 10 Hz (operation S1110). However, this is not limiting.

The processor 140 may process acceleration data via an IIR SOS filter and, then, acquire the sum of three-axis data (operation S1120). A bandwidth of the IIR filter may be 0.5 Hz and pOutput_ACC_Sum [g_nRawDataCnt]=Abs (Filter (X)+Abs(Filter(X))+Abs(Filter(X))). However, this is not limiting.

Similarly to operation S1110 and operation S1120, the acceleration data may be collected and feature data extraction and sleeping stage estimation may be performed.

In detail, the processor 140 may determine whether the number of data for 30 seconds is greater than or equal to 300 (operation S1130). That is, g_nRawDataCnt==SAMPLE_DATA_LENGTH (=300) may be satisfied. One epoch is 30 seconds and a sampling frequency of 10 Hz is used and, thus, 300 data is required. However, this is not limiting.

When the number of data for 30 seconds is not greater than or equal to 300 (operation S1130, N), the method may return back to operation S1110.

When the number of data for 30 seconds is greater than or equal to 300 (operation S1130, Y), the processor 140 may apply a weight to data of the sum result to calculate a median algorithm and average calculation in order to extract the feature data (operation S1140). The feature data may be extracted based on Activity=0.4*median (sum_data)+ 0.6*mean (sum_data).

The processor 140 may determine whether a length of activity is greater than or equal to 10 epochs (operation S1150). This may be based on the case in which a minimum epoch for estimating an awakening stage, i.e., the awakening stage, is set to 10 epochs. However, this is not limiting.

When the length of activity is not greater than or equal to 10 epochs (operation S1150, N), the method may return back to operation S1110.

When the length of activity is greater than or equal to 10 epochs (operation S1150, Y), the processor 140 may align data of previous feature data of 5 epochs and current feature data of 10 epochs in one memory and apply a smoothing algorithm (a window size is fixed to 10) (operation S1160). The smoothing algorithm may be processed and, then first 5 epochs of a memory may be deleted. However, this is not limiting.

The processor 140 may determine whether the length of feature data to which smoothing is applied is equal to 15 epochs (operation S1170). In this step, since the smoothing algorithm is used during the previous operation, 5 epochs may be further received and calculated. However, this is not limiting.

When the length of feature data to which smoothing is applied is not equal to 15 epochs (operation S1170, N), the method may return back to operation S1110.

When the length of feature data to which smoothing is applied is equal to 15 epochs (operation S1170, Y), the processor 140 may determine whether a value of the feature data to which smoothing is applied is greater than or equal to a specific movement value (operation S1180).

When the value of the feature data to which smoothing is applied is greater than or equal to the specific movement value (operation S1180, Y), the processor 140 may determine a current state as an awakening stage (operation S1190).

When the value of the feature data to which smoothing is applied is not greater than or equal to the specific movement value (operation S1180, N), the processor 140 may set a threshold in order to determine an awakening stage and a sleep state (operation S1191).

Threshold 1 may be set using an average value of the smoothed feature data and a previous threshold value; Threshold 1=(Mean(pFeatureData_Smooth, FEATURE_SIZE)+g_dUpdata_Threshold)/2.0. However, this is not limiting.

Threshold 2 may be set using data of previous 2 epochs; Threshold 2=((pFeatureData_Smooth[i−2]+pFeatureData_Smooth[i−1]/2.0)+0.5. However, this is not limiting.

The processor 140 may determine whether feature data to which smoothing is applied is less than the two thresholds (operation S1192). Two conditions are as follows.

Condition 1=(pFeatureData_Smooth[i]<g_dThreshold+ (g_dThreshold*0.15)
Condition 2=(pFeatureData_Smooth[i]<Threshold2)

When feature data to which smoothing is applied is not less than the two thresholds (operation S1192, N), the processor 140 may determine a current state as an awakening stage (operation S1193).

When feature data to which smoothing is applied is less than the two thresholds (operation S1192, Y), the processor 140 may determine a current stage as a NREM sleeping stage (operation S1194).

FIG. 12 is a flowchart of estimated stage correction and final result deduction.

Referring to FIG. 12, upon resetting and starting an awakening stage region, the processor 140 may set 10 epochs as Wake (operation S1210); pEstimated_Wake [0:9]= Wake. However, this is not limiting.

A period in which a high value of feature data is continuously shown in an awakening stage may be set to '0' in an awakening stage and may be changed to a NREM sleeping stage. When wake is continuously generated in 5 epochs or more in a wake state group, either side of wake states of the wake state group may be set to '0' and changed to a NREM sleeping stage.

The processor 140 may determine whether wake and sleep simultaneously occur in the same epoch (operation S1220).

When wake and sleep simultaneously occur in the same epoch (operation S1220, Y), priority may be applied to wake (operation S1230).

When wake-up and sleeping do not simultaneously occur in the same epoch (operation S1220, N), the processor 140 may change an unknown period such that a previous event is subsequent to the period (operation S1240).

The processor 140 may generate a final event according to pEstimated_Wake+pEstimated_Sleep (operation S1250). In this case, first 5 epochs 10 epochs of final event may be determined as a true value. A stage value of fifth epoch may return to result data. However, this is not limiting.

Figure 13:
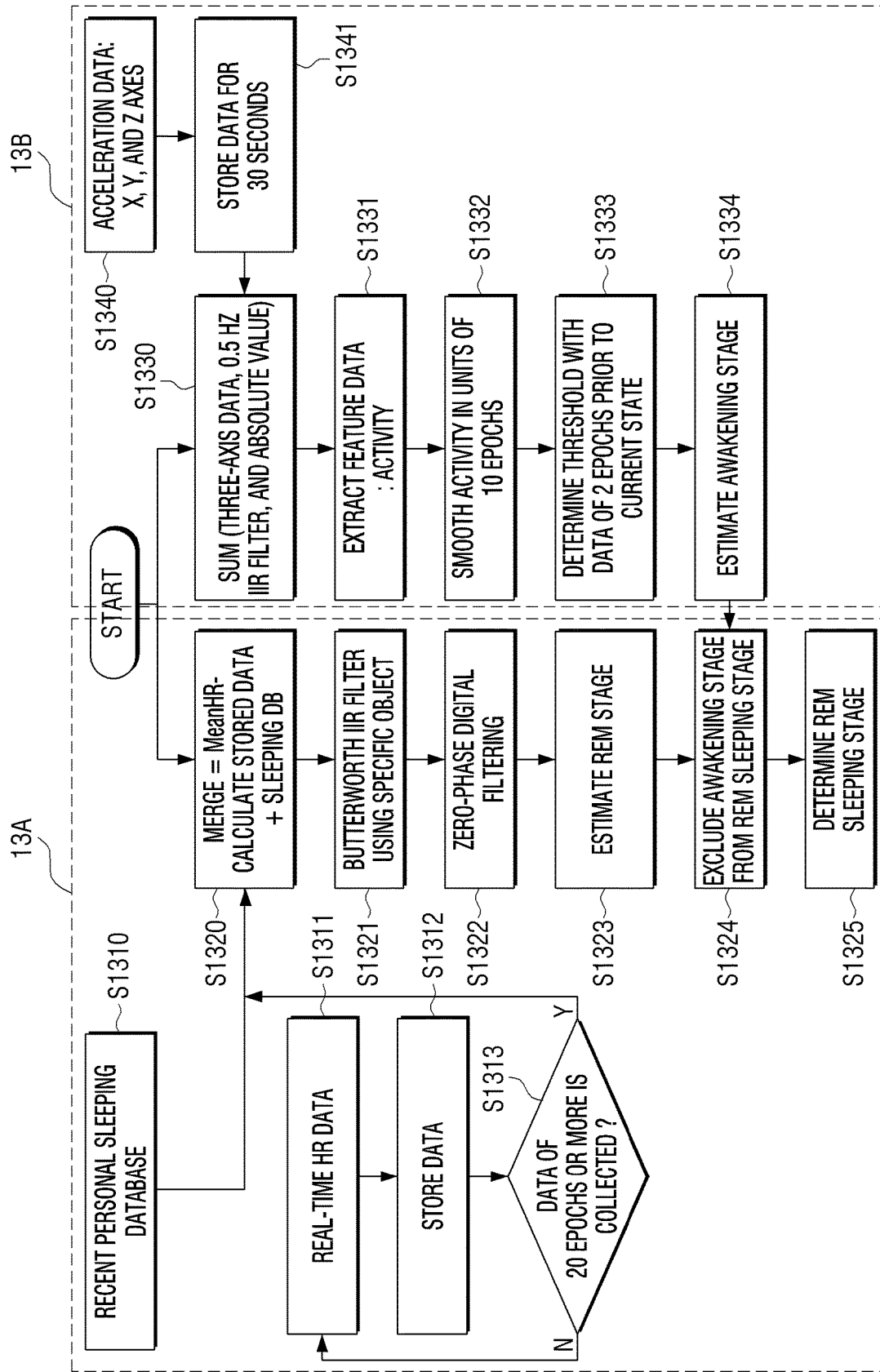
FIG. 13 is a flowchart of a method of a method of analyzing a sleeping state of an electronic device according to an exemplary embodiment.

FIG. 13 is a flowchart of a method of analyzing a sleeping state of the electronic device 100 according to another exemplary embodiment.

Referring to FIG. 13, a block 13A relates to a method of estimating a REM sleeping stage and a block 13B relates to a method of a estimating an awakening stage and a method of acquiring sleep efficiency in real time or near real time.

Here, Epoch Length is 30 seconds and a used signal is ECG (Heart Rate, 20% of period per epoch is used). However, this is not limiting.

In estimation of a REM sleeping stage, a recent personal sleeping database may be used (operation S1310). The recent personal sleeping database may be configured by MeanHR and may be used when sleep efficiency is 70% or more. However, this is not limiting.

The processor 140 may collect real-time HR data (operation S1311), store data (operation S1312), and determine whether data of 20 epochs or more is collected (operation S1313). However, this is not limiting. When data of 20 epochs or more is not collected (operation S1313, N), the method may return back to operation S1311.

When data of 20 epochs or more is collected (operation S1313, Y), the processor 140 may MeanHR-calculate the stored data and merge the calculated data with a sleeping DB (operation S1320).

The processor 140 may perform Butterworth IIR filter design using a specific object (operation S1321). The processor 140 may perform Zero-phase digital filtering (0.1 to 0.5 Hz) (operation S1322). However, this is not limiting. The processor 140 may estimate a REM sleeping stage (operation S1323).

The processor 140 may collect acceleration data in X, Y, and Z axes (operation S1340). The processor 140 may store data for 30 seconds (logic is performed in a unit of 1 epoch) (operation S1341). However, this is not limiting.

The processor 140 may calculate SUM (three-axis data, 0.5 Hz IIR Filter, and absolute value) according to sum_data=[abs(Y)+abs(Z)] (operation S1330). However, this is not limiting.

The processor 140 may extract feature data (operation S1331). In detail, the feature data may be extracted based on Activity=0.4*median (sum_data)+0.6*mean(sum_data).

The processor 140 may smooth (Moving Average) Activity in a unit of 10 epochs (operation S1332).

The processor 140 may determine a threshold with data of 2 epochs prior to a current state (operation S1333). However, this is not limiting. An awakening stage may be estimated (operation S1334). Based on the result, the awakening stage is excluded from the REM sleeping stage (operation S1324).

The processor 140 may finally estimate a REM sleeping stage (operation S1325). In this case, only a previous stage of 10 epochs may be used. However, this is not limiting.

That is, input data of the aforementioned algorithm may use average HR data and only a period of 20% per 1 epoch (30 seconds) may be used in calculation. However, this is not limiting. A recent user sleeping DB may use data including average HR and use only a data group with sleep efficiency of 70% or more. However, this is not limiting.

In detail, the aforementioned algorithm may estimate a REM sleeping stage using average HR and estimate an awakening stage using acceleration data. The awakening stage may be set with higher priority than the REM sleeping stage and a period that is not the awakening stage or the REM sleeping stage may be set as a deep sleep period. A REM extraction algorithm may include extracting feature to estimate a REM sleeping stage and performing a post-processing procedure to acquire a REM region. Wake region detection may include extracting feature like the REM extraction procedure and then executing a moving average function every 10 epochs to determine a threshold. However, this is not limiting. The wake region may be calculated based on the threshold. After this procedure is completely performed, the number of wake states may be estimated to acquire sleep efficiency and a sleeping stage result may be output. In an exemplary embodiment, a sleeping state might not be recognized for first 10 minutes and a current sleeping state may be recognized after 5 minutes. Accordingly, a delay time for outputting the user sleeping state analysis result may be from 5 to 10 minutes or less. However, this is not limiting.

For example, the recent sleeping information of a user is displayed on the electronic device 100 or the user terminal device 200 and is used in algorithm calculation to acquire reusability of a memory. While a user sleeps, the electronic device 100 may control other various electronic devices. When a battery of the electronic device 100 is insufficient, measurement time of a heart rate monitoring (HRM) sensor may be manually or automatically adjusted and, thus, a sleeping state is also used while the battery is effectively used.

The exemplary embodiments may be embodied by a computer or similar device readable recording medium using software, hardware, or a combination thereof. In a hardware configuration, an exemplary embodiment may be achieved by at least one of application specific integrated circuits (ASICs), digital signal processors (DSPs), digital signal processing devices (DSDPs), programmable logic devices (PLDs), field programmable gate arrays (FPGAs), processors, controllers, microprocessors, and an electronic unit for other functions. In some cases, exemplary embodiments may be embodied as the processor 140 without changes. In a software configuration, exemplary embodiments such as a procedure and a function may be embodied as separate software modules. Each of the software modules may perform one or more functions and operations described in the specification.

The method of controlling an electronic device according to the various exemplary embodiments may be stored in a non-transitory readable medium. The non-transitory readable medium may be installed and used in various devices.

The non-transitory computer-readable medium is a medium that semi-permanently stores data and from which data is readable by a device, but not a medium that stores data for a short time, such as register, a cache, a memory, and the like. In detail, programs for executing the aforementioned various methods may be stored in the non-transitory computer-readable medium, for example, a compact disc (CD), a digital versatile disc (DVD), a hard disc, a Blu-ray disc, a universal serial bus (USB), a memory card, a read only memory (ROM), and the like.

The foregoing exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. An electronic device comprising:
   a first sensor for generating a movement signal corresponding to a user movement;
   a second sensor configured to physically contact a user to generate a photoplethysmography (PPG) signal, the second sensor comprising:
   a light emitter for emitting light for generating the PPG signal, and
   a light receiver for receiving light reflected from the user;
   a communicator; and
   a processor configured to:
   set a plurality of preset time periods which are consecutive time periods for analyzing a sleep of the user, each of the plurality of preset time periods being a predetermined amount of time to determine one sleeping state of the user,
   set a first part of the predetermined amount of time in each of the plurality of preset time periods to emit the light, and set a remaining part of the predetermined amount of time in each of the plurality of preset time periods to not emit the light,
   control the light emitter to emit the light in the first part of each of the plurality of preset time periods and to not emit the light in the remaining part of each of the plurality of preset time periods, and
   determine, for each of the plurality of preset time periods, the sleeping state of the user based on the movement signal and the PPG signal that are generated for each of the plurality of preset time periods, respectively,
   wherein the first part of the predetermined amount of time and the remaining part of the predetermined amount of time are variably set based on a charge state of a battery of the electronic device.

2. The electronic device as claimed in claim 1, wherein the processor is further configured to determine the sleeping state of the user as any one of an awakening stage, a non-rapid eye movement (NREM) sleeping stage, and a rapid eye movement (REM) sleeping stage.

3. The electronic device as claimed in claim 1, wherein the processor is further configured to smooth the PPG signal generated for one of the plurality of preset time periods using the PPG signal generated prior to the one of the plurality of preset time periods, and compare the smoothed PPG signal with a certain value to determine the sleeping state of the user in the one of the plurality of preset time periods.

4. The electronic device as claimed in claim 1, further comprising a touch screen for receiving a sleep analysis start command,
   wherein the processor is further configured to control the first sensor and the second sensor to generate the movement signal and the PPG signal, respectively, based on the sleep analysis start command being received.

5. The electronic device as claimed in claim 4, wherein the touch screen is further configured to receive a sleep analysis termination command, and calculate a sleep efficiency from a first time point at which the sleep analysis start command is received, to a second time point at which the sleep analysis termination command is received, based on the sleep analysis termination command being input.

6. The electronic device as claimed in claim 1, wherein the first sensor comprises at least one from among an acceleration sensor, a gyro sensor, and a gravity sensor.

7. The electronic device as claimed in claim 1, wherein the processor is further configured to control the communicator to transmit a control command corresponding to the determined sleeping state of the user to another electronic device to cause the another electronic device to operate in correspondence with the determined sleeping state of the user.

8. The electronic device as claimed in claim 1, wherein the processor is further configured to determine whether an operation state of another electronic device is to be changed based on the sleeping state of the user determined in each of the plurality of preset time periods, and control the communicator to transmit a control command corresponding to a changed operation state to the another electronic device based on the determining that the operation state of the another electronic device is to be changed based on the determined sleeping state of the user in a certain preset time period.

9. The electronic device as claimed in claim 1, wherein the electronic device comprises a user-wearable device.

10. The electronic device as claimed in claim 1, wherein the processor is further configured to divide the predetermined amount of time in each of the plurality of preset time periods into the first part with a consecutive time span beginning at a start of the predetermined amount of time in each of the plurality of preset time periods and the remaining part with the consecutive time span beginning at a stop of the first part in each of the plurality of preset time periods and ending at a stop of the predetermined amount of time in each of the plurality of preset time periods, so that the first part forms an initial part of each of the plurality of preset time periods and the remaining part follows the first part in time and forms the remaining part at an end of each of the plurality of preset time periods.

11. A method comprising:
   setting a plurality of preset time periods which are consecutive time periods for analyzing a sleep of a user, each of the plurality of preset time periods being a predetermined amount of time to determine one sleeping state of the user;

generating a movement signal based on a user movement, by a first sensor of an electronic device;

generating a photoplethysmography (PPG) signal by a second sensor of the electronic device, wherein the second sensor emits light for generating the PPG signal while physically contacting the user, the generating the PPG signal comprising:
- setting a first part of the predetermined amount of time in each of the plurality of preset time periods to emit the light, and setting a remaining part of the predetermined amount of time in each of the plurality of preset time periods to not emit the light,
- controlling a light emitter of the second sensor to emit the light in the first part of each of the plurality of preset time periods and to not emit the light in the remaining part of each of the plurality of preset time periods, and
- receiving, by a light receiver of the second sensor, light reflected from the user; and
- determining, for each of the plurality of preset time periods, the sleeping state of the user based on the movement signal and the PPG signal that are generated for each of the plurality of preset time periods, respectively, wherein the first part of the predetermined amount of time and the remaining part of the predetermined amount of time are variably set based on a charge state of a battery of the electronic device.

12. The method as claimed in claim 11, wherein the determining the sleeping state of the user comprises determining the sleeping state as any one of an awakening stage, a non-rapid eye movement (NREM) sleeping stage, and a rapid eye movement (REM) sleeping stage.

13. The method as claimed in claim 11, wherein the determining the sleeping state of the user further comprises:
- smoothing the PPG signal generated for one of the plurality of preset time periods using the PPG signal generated prior to the one of the plurality of preset time periods; and
- comparing the smoothed PPG signal with a certain value to determine the sleeping state of the user in the one of the plurality of preset time periods.

14. The method as claimed in claim 11, further comprising:
- receiving a sleep analysis start command; and
- controlling the first sensor and the second sensor to generate the movement signal and the PPG signal, respectively, based on the sleep analysis start command being received.

15. The method as claimed in claim 14, further comprising:
- receiving a sleep analysis termination command; and
- calculating a sleep efficiency from a first time point at which the sleep analysis start command is received, to a second time point at which the sleep analysis termination command is received, based on the sleep analysis termination command being input.

16. The method as claimed in claim 11, wherein:
the first sensor includes at least one from among an acceleration sensor, a gyro sensor, and a gravity sensor.

17. The method as claimed in claim 11, further comprising:
- transmitting a control command corresponding to the determined sleeping state of the user to another electronic device to cause the another electronic device to operate in correspondence with the determined sleeping state of the user.

18. The method as claimed in claim 17, wherein the determining the sleeping state of the user further comprises:
- determining whether an operation state of the another electronic device is to be changed based on the sleeping state of the user determined in each of the plurality of preset time periods, and
- the transmitting comprises transmitting the control command corresponding to a changed operation state to the another electronic device based on the determining that the operation state of the another electronic device is to be changed based on the determined sleeping state of the user in a certain preset time period.

* * * * *